United States Patent [19]

McGuire

[11] Patent Number: 4,598,047

[45] Date of Patent: Jul. 1, 1986

[54] PHENYLALANINE AMMONIA LYASE-PRODUCING MICROBIAL CELLS

[75] Inventor: Jeffrey C. McGuire, Frederick, Md.

[73] Assignee: Genex Corporation, Rockville, Md.

[21] Appl. No.: 624,285

[22] Filed: Jun. 25, 1984

[51] Int. Cl.$^4$ .......... C12P 13/22; C12N 9/88; C12N 1/36; C12N 1/20; C12N 1/16
[52] U.S. Cl. .................. 435/108; 435/232; 435/245; 435/255; 435/253
[58] Field of Search ............ 435/232, 245, 255, 108

[56] References Cited

U.S. PATENT DOCUMENTS 3,654,079  4/1972  Tanaka et al. ............ 435/108
3,660,235  5/1972  Okumura et al. .......... 435/108
3,909,353  9/1975  Tsuchida et al. .......... 435/108

FOREIGN PATENT DOCUMENTS 1489468  10/1977  United Kingdom .

OTHER PUBLICATIONS

Biotechnology and Bioengineering, vol. 22, pp. 651–654 (1980).
Wang et al., Fermentation and Enzyme Technology 1979, pp. 53, 54.
Yamada et al., *Applied and Environmental Microbiology*, Nov. 1961, vol. 42, No. 5, pp. 773–778.
Loureiro-Dias, *Applied and Environmental Microbiology*, Sep. 1982, vol. 44, No. 4, pp. 744–746.
Nakamichi et al., *Applied Microbiology and Biotechnology*, 1983, Rev. 2/10/83, pp. 158–162, vol. 18.
LaManna and Mallette, *Basic Bacteriology*, 2nd Ed. 1959, pp. 626–649.

*Primary Examiner*—Lionel M. Shapiro
*Attorney, Agent, or Firm*—Bernard, Rothwell & Brown

[57] ABSTRACT

A method for producing and isolating catabolite resistant, phenylalanine ammonia-lyase-producing microorganisms is disclosed. Also disclosed are novel catabolite resistant organisms and a method for producing L-phenylalanine using such organisms.

9 Claims, 2 Drawing Figures

PHENYLALANINE AMMONIA LYASE-PRODUCING MICROBIAL CELLS

BACKGROUND OF THE INVENTION

The present invention relates to novel phenylalanine ammonia-lyase-producing microorganisms and methods for their selection, production, and use. More particularly, the invention concerns microorganisms which produce relatively high levels of the enzyme, phenylalanine ammonia-lyase (hereinafter sometimes called PAL), which in turn, is useful for the production of L-phenylalanine.

L-phenylalanine is an essential amino acid in man, and is, therefore, an important ingredient of enteral and parenteral nutritional formulations. In addition, this amino acid is useful as a starting material for the production of other products, such as the artificial sweetener, aspartame. Various microbial processes for the production of phenylalanine are known. For example, U.S. Pat. No. 3,660,235 describes the production of phenylalanine by phenylalanine analog resistant strains of Brevibacterium, Corynebacterium, Arthrobacter, Bacillus and Candida. The production of this amino acid by tyrosine-requiring mutants of certain strains of Brevibacterium, Corynebacterium, Arthrobacter, and Escherichia is also known. See U.S. Pat. Nos. 3,654,079 and 3,909,353.

PAL catalyzes the breakdown of L-phenylalanine to trans-cinnamic acid and ammonia. This enzymatic reaction is reversible, and British Patent No. 1,489,468 discloses a process for the production of L-phenylalanine which involves the PAL-catalyzed reaction of trans-cinnamic acid with ammonium ions to yield L-phenylalanine. This reaction has been found to be a useful procedure for producing L-phenylalanine, and therefore, there is a continuing need to obtain production microorganisms which produce high levels of PAL activity. Such microorganisms can be used directly for the conversion of cinnamic acid and ammonium ions to L-phenylalanine, or the enzyme can be isolated from the cells and used to produce L-phenylalanine in various forms of bioreactors.

One problem that has been associated with the microbial production of PAL is that its biosynthesis is repressed by carbon catabolites. The induction of PAL biosynthesis therefore requires media that are substantially free of glucose or other simple carbohydrate nutrients. Since the growth media used for cultivating microbial cells to a satisfactory cell density advantageously contain glucose or other carbohydrates, it has heretofore been necessary to remove those nutrients prior to PAL induction. Such removal has generally been accomplished by permitting the cells to consume substantially all available carbohydrate nutrients prior to induction. An alternative procedure has been to separate the cells from their growth medium and resuspend them in a catabolite-free induction medium. PAL production could be simplified and facilitated by using PAL-producing cells that are resistant to catabolite repression.

SUMMARY OF THE INVENTION

In accordance with the present invention, catabolite resistant, PAL-producing mutants are selected by growing them on a minimal nutritional medium containing 2-deoxyglucose and containing L-phenylalanine, as substantially the sole carbon source. A high proportion of mutants which grow on such a medium are catabolite resistant and produce PAL in the presence of glucose or other simple carbohydrates. This technique can be used to select catabolite resistant strains of any PAL-producing microorganism, and has been particularly useful in obtaining yeast mutants of the genera, Rhodotorula and Rhodosporidium. These cells may be used for the direct conversion of cinnamic acid and ammonium ions to phenylalanine, or alternatively, can be grown to produce high levels of PAL, which is subsequently employed for the production of L-phenylalanine.

DETAILED DESCRIPTION OF THE INVENTION

Figure 1:
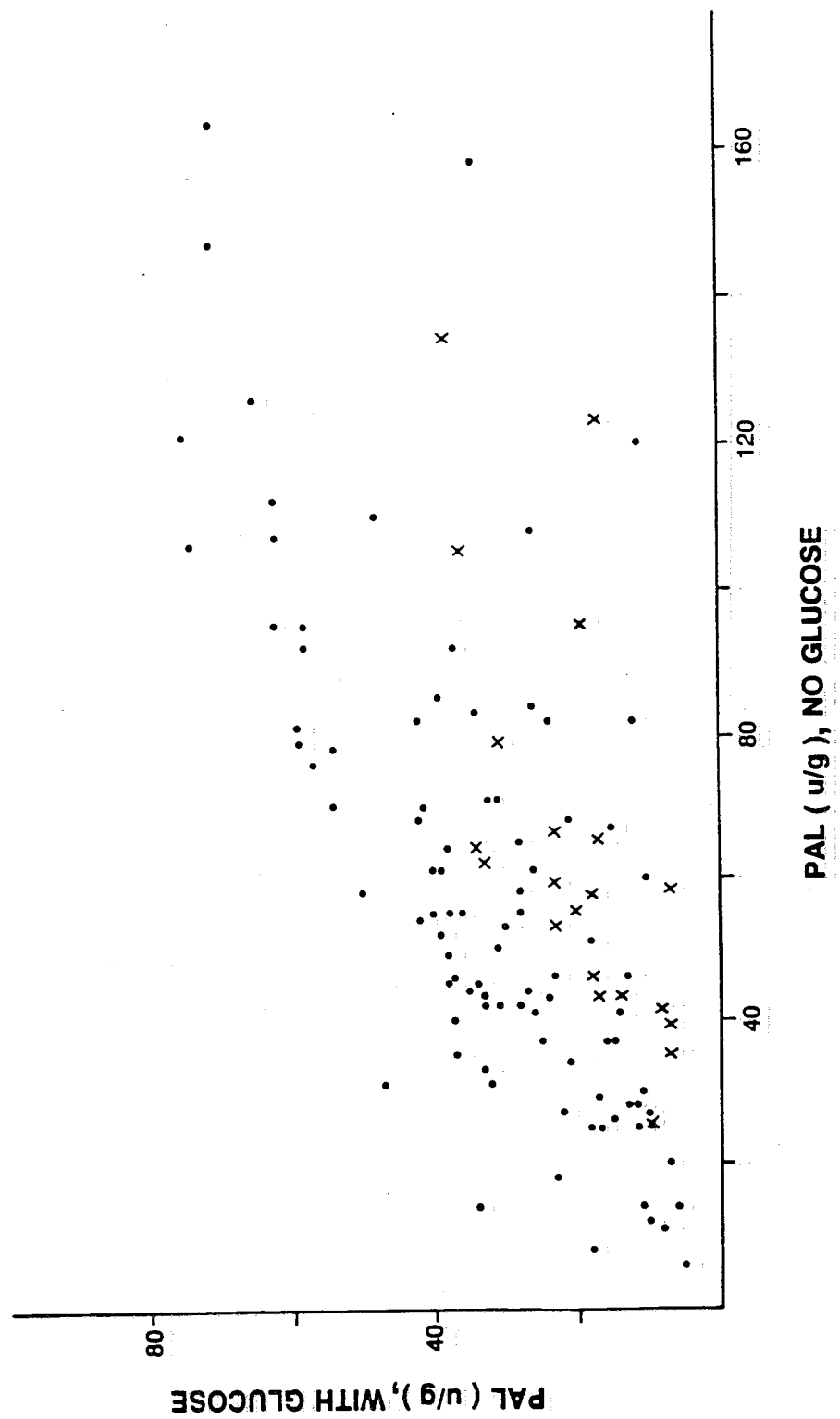
FIG. 1 is a graph in which PAL activities in induced R. rubra cells in medium containing phenylalanine and 5 mg/ml glucose are plotted against PAL activities in induced cells in glucose-free medium. Each point represents a different isolate and the x's represent values observed for the parent R. rubra strain included as a control.

The microbial strains of the present invention are obtained by conventional mutation procedures. Such procedures include, for example, exposing a culture of a parent strain to chemical mutation, using a mutagen such as nitrosoguanidine, ethylmethane sulfonate, 5-bromouracil, hydroxylamine, nitrogen and sulfur mustards, and the like. Irradiating the cells with ultraviolet light or ionizing radiation can also be employed. Such techniques are well known, and are described, for example, in "Basic Bacteriology", La Manna and Mallette, Second Edition, the Williams & Williams Company, Baltimore, 1959, on pages 646 to 649.

Chemical or radiation induced mutation typically produces hundreds to thousands of mutant strains. Selecting viable strains that have the desired characteristics is an arduous task, unless a specific selection procedure can be devised. The present invention involves a selection procedure for catabolite resistant PAL-producing mutants, wherein the mutants are grown on a minimal nutrient medium containing 2-deoxyglucose and L-phenylalanine, as substantially the sole carbon source. 2-deoxyglucose is an analog of glucose which, like glucose, has been found to repress the biosynthesis of PAL, but unlike glucose, cannot be utilized by microorganisms as a nutrient. Cells which can utilize L-phenylalanine as a carbon source in the presence of 2-deoxyglucose must produce PAL, as that enzyme is required for the first step in the catabolism of phenylalanine. Confirmation of the PAL-producing capabilities of cells can be achieved by enzyme activity measurements.

Microbial cells that can be obtained by these procedures include bacteria of the genus Streptomyces and yeasts of the genera Rhodotorula, Rhodosporidium, and Sporobolomyces. After producing mutants from wild-type or known PAL-producing strains, the mutant population is inoculated into a minimal essential medium containing 2-deoxyglucose and a growth-supporting amount of L-phenylalanine. The base minimal medium contains essential vitamins, minerals and a source of nitrogen, but does not contain sufficient quantities of a source of carbon to support microbial growth. Generally, concentrations of L-phenylalanine of from about 1 to about 10, preferably from about 3 to about 7 grams per liter of medium are employed. The 2-deoxyglucose is employed in a normally growth-inhibiting concentration. Such concentration of 2-deoxyglucose in the selective medium is generally an amount that would substantially inhibit PAL biosynthesis in wild type strains. Normally inhibiting concentrations typically range from about 0.03 to about 1.0 mg of 2-deoxyglucose per ml. of medium, preferably from about 0.07 to about 0.5 mg/ml.

Minimal essential media are well known, and typically include phosphate, sulfate, chloride, iodide and molybdate salts of potassium, sodium, iron, manganese, and zinc in concentrations of from about 0.05 to about 1.0 grams per liter. In addition, these media advantageously contain vitamins and growth factors, such as biotin, calcium pantothenate, folic acid, inositol, niacin, p-aminobenzoic acid, pyridoxine hydrochloride, riboflavin, and thiamine hydrochloride in amounts ranging from about 0.1 to about 1.0 milligrams per liter. The composition of the medium is not critical, and may be composed of a variety of synthetic, semi-synthetic or natural ingredients.

The selection media are preferably solid media (e.g., agar media) to facilitate handling and transfer of cells. These media are sterile and are buffered to a physiologically acceptable pH, e.g. from about 5 to about 8, preferably from about 6 to about 7. Inoculated media are incubated at biologically acceptable temperatures, e.g., from about 20° C. to about 50° C., preferably about 30° C.

Microbial colonies which grow on a selective 2-deoxyglucose medium are advantageously collected and re-cultivated on that medium one or more times to generate pure cultures of catabolite resistant strains. Mutants which are selected by these procedures can be evaluated quantitatively by cultivating them in PAL induction media (containing phenylalanine) in the presence and absence of glucose. PAL activity of the cells can be measured by standard procedures, and the ratio of PAL production in the glucose-free medium to PAL production in the glucose medium can be used as an indication of the catabolite resistance of mutant strains. Such ratios for commercial PAL production strains used heretofore have been about 3.7, whereas mutants selected in accordance with the present invention produce ratios below about 2.0 and preferably below about 1.3.

Several mutant strains of the yeast, *Rhodotorula rubra*, produced in accordance with the present invention have been found particularly preferred for the production of PAL. These strains have been designated as follows and deposited with the ARS Culture Collection, U.S. Department of Agriculture, Peoria, Ill. with the indicated accession numbers:

| Strain Designation | NRRL No. |
|---|---|
| GX 5902 | Y-15779 |
| GX 5903 | Y-15780 |
| GX 5904 | Y-15781 |

The catabolite resistant, PAL-producing strains of this invention can be used to produce PAL by fermentation, and the PAL can in turn be used to produce L-phenylalanine from t-cinnamic acid and ammonia. Generally, PAL is produced by cultivating a PAL-producing strain in a nutritional medium containing assimilable sources of carbon and nitrogen and essential vitamins, minerals and other growth factors. Suitable carbon sources can include various refined or crude carbohydrates such as glucose, sucrose, molasses, starches, grains and the like. A preferred carbon source is glucose syrup. Nitrogen sources include inorganic ammonium salts, such as ammonium phosphates, ammonium sulfate, ammonium acetate, ammonium citrate, ammonium nitrate and the like and organic nitrogeneous substances such as soybean meal, meat infusion, amino acids, corn steep liquor, protein hydrolyzates, peptones, yeast extracts, and the like. A preferred nitrogen source for the process of this invention is yeast extract.

Vitamins, minerals and other growth factors may be supplied by the carbon and nitrogen sources, or may be provided separately. These components can vary with the particular microorganism employed. Typically, trace minerals such as zinc, manganese, iron, cobalt, and calcium can be supplied in growth-promoting amounts as inorganic salts. These minerals may, for example, be supplied with process water, e.g. tap water, sea water, etc. Another growth factor typically supplied is DL-methionine. Nutrient media of the type described are well known, and can vary in composition widely.

Because of the inducible nature of the PAL enzyme in most microorganisms, the cells are conveniently grown to a desired cell density in a conventional medium as described above. After the desired cell growth has been achieved, a PAL inducer can be added to stimulate PAL synthesis. L-phenylalanine is a good PAL inducer, and a number of analogs of L-phenylalanine also induce the synthesis of this enzyme. For example L-tyrosine, L-phenylalanine methylester, or m-fluoro-DL-phenylalanine, can be employed for this purpose.

The PAL inducer is added to the cells in a PAL-inducing amount, which generally ranges from about 0.1 to about 1.0 g/g of cells (dry weight). Preferably, the PAL inducer is employed at a concentration from about 0.2 to about 0.5 g/g of cells (dry weight). During this step, PAL-inducing conditions of temperature, pH, and aeration are maintained. These parameters may vary, and are generally maintained within physiologically compatible limits.

The cells are advantageously cultivated under PAL-inducing conditions until the PAL activity reaches about 0.5–2.0 units per ml, preferably about 1.5 units per ml. It has generally been observed that under these conditions, the PAL activity increases to a certain point and then begins to diminish. PAL produced by these procedures may be employed to produce L-phenylalanine from t-cinnamic acid and ammonia. These reactants can be added directly to the PAL-containing cells in an aqueous medium, or the cells or enzyme isolated therefrom can be immobilized by known procedures on a solid support that can be reused for so long as the enzyme activity is maintained.

Phenylalanine is produced by this method under phenylalanine-producing conditions. These conditions will vary, depending upon the particular microbial strains employed, whether whole cells or cell-free enzyme preparations are used and whether immobilized systems are employed. In general, t-cinnamic acid and aqueous ammonia (or soluble ammonium salts) are supplied in amounts such that aqueous ammonia or ammonium salts are in excess. Aqueous ammonia and ammonium salts are employed in amounts from about 3 to about 8 moles per liter. The purpose of the high ammonia concentration is to obtain a high rate of conversion of t-cinnamic acid into phenylalanine. The t-cinnamic acid is employed in amounts of from about 5 to about 30 grams per liter. The concentration of t-cinnamic acid in the reactor is maintained within these ranges by periodic additions of t-cinnamic acid. The pH is advantageously maintained within the range of 9.5–11, preferably 10.4–10.8. The temperature is generally maintained within the range of 15°–35° C.

L-phenylalanine produced by these methods can be recovered by any suitable means. The solubility of this amino acid is relatively low, therefore, often the product will precipitate from the reaction mixture when the pH is adjusted to its isoelectric point (5.5), and can be recovered by filtration or centrifugation. The product can then be further purified, if desired, by recrystallization or column chromatography.

This invention is further illustrated by the following examples, which are not intended to be limiting.

GENERAL PROCEDURE

*Rhodotorula rubra* strain GX3243, NRRLY-15597, was the starting strain for the experiments described below. Strains were maintained on YPD agar (see below). Growth in liquid culture was followed by monitoring optical density at 560 nm. An optical density of 1.0 corresponds to about 0.37 g/L dry cell weight. Cultures were incubated at 30° C.

Media

YE medium contained 15 g of yeast extract per liter. YPD medium contained 20 g per liter of Bacto-Peptone (Difco Laboratories, Detroit, Michigan USA), 10 g per liter of yeast extract, and 20 g per liter of glucose. PA medium contained, per liter, 5 g L-phenylalanine, 5 g ammonium sulfate, 1 g potassium phosphate, 0.5 g magnesium sulfate, 0.1 g sodium chloride, 0.1 g calcium chloride, and 0.4 mg each of biotin, calcium pantothenate, folic acid, inositol, niacin, para-amino benzoic acid, pyridoxine hydrochloride, riboflavin, thiamine hydrochloride, boric acid, potassium iodide, ferric chloride, manganous sulfate, sodium molybdate, and zinc sulfate. Solid media contained 20 g of agar per liter, in addition to the above components.

Mutagenesis

Cultures grown in YPD or YE medium were centrifuged and resuspended in PA medium at an optical density of 1. Ethylmethane sulfonate (EMS) was added to a final concentration of 5 mg/ml. After exposure to EMS for 60 minutes at 30° C., cells were washed and plated.

PAL Induction

For PAL induction, strains were inoculated from agar plates into 5 ml of YPD medium in test tubes and incubated at 30° C. with shaking. After two or three days (final O.D. at 560 nm was 5–15), the cultures were centrifuged at 6000×g for 10 minutes. The cell pellets were resuspended in 10 ml of PA medium at an optical density of 1.0. The cultures were then incubated at 30° with shaking for four and a half to seven hours. PAL activity and optical density were then measured as described in the following section.

PAL Assay

PAL was measured by adding a sample of cells (10–100 microliters) to 1 ml of a solution of 50 mM Tris buffer (pH 8.8), 25 mM L-phenylalanine, and 0.001% (wt/vol) of cetylpyridinium chloride. This mixture was incubated in a recording spectrophotometer and the appearance of cinnamic acid was followed at 280 nm (molar absorbance =16,200). The rate of increase in optical density was measured during a period of linear increase, ususally between one and five minutes after addition of cells. A unit of PAL is the amount of enzyme catalyzing the formation of 1 micromole of cinnamic acid per minute at 30° C. Specific activities are expressed as units of PAL per gram of dry cellweight (U/g).

EXAMPLE I

*R. rubra* cells were mutagenized with ethylmethane sulfonate as described above. Mutagenized cells were plated on PA agar containing 2-deoxyglucose (0.1 mg/ml) and incubated at 30° C. Aliquots of unmutagenized cells were also plated on this medium. After incubation for 11 to 15 days, colonies that appeared on the 2-deoxyglucose plates were picked and restreaked on the same medium. After 7–15 days of incubation, isolates were again picked and restreaked. Isolates from the final plating were tested for induction of PAL in the absence and presence of 5 mg/ml of glucose using the PAL Induction procedure described above.

The results of the inductions are shown in FIG. 1, in which PAL activities in the phenylalanine+glucose media are plotted vs. PAL activities in the glucose-free media. Each point represents a different isolate and the x's represent values observed for the parent *R. rubra* strain which was included as a control on most days. The variability in PAL induction is apparent from the scattered pattern of x's. A total of 94 isolates were tested; five from unmutagenized *R. rubra*, 89 from mutagenized cells. Isolates prepared in this manner averaged significantly higher PAL titers in the presence of glucose than the parent strain.

EXAMPLE II

Figure 2:
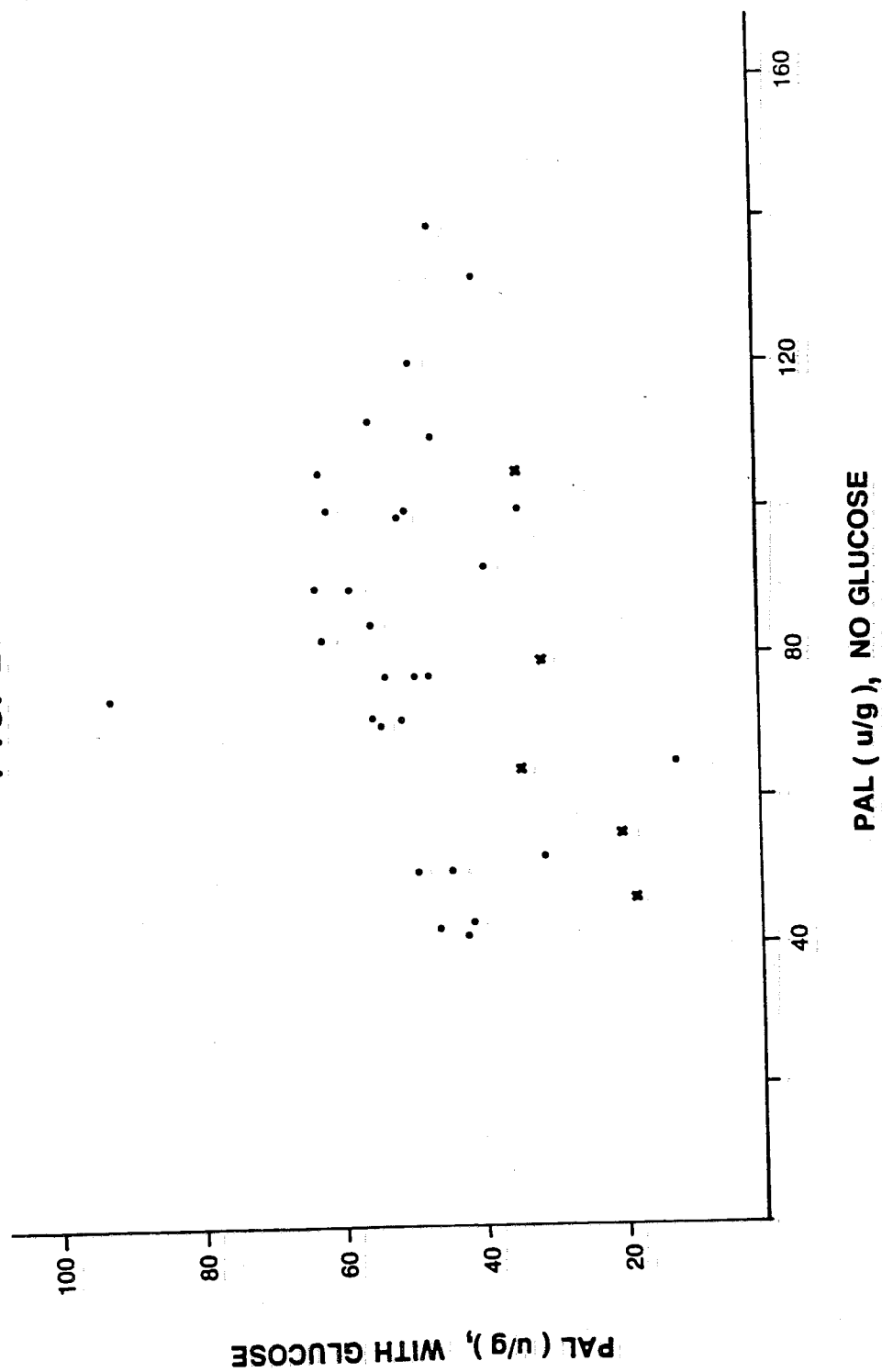
FIG. 2 is a graph in which PAL activities in induced R. rubra cells in medium containing phenylalanine and 10 mg/ml glucose are plotted against PAL activities in glucose-free medium. The 29 isolates represented in FIG. 2 were chosen on the basis of the data in FIG. 1 with 4 isolates being derived from the unmutagenized parent strain, and 25 isolates from mutagenized cells.

On the basis of the data shown in FIG. 1, 29 isolates were selected for retesting. Of these isolates, four were from unmutagenized parent strain, 25 were from mutagenized cells. Some isolates were chosen on the basis of their high PAL titers in the absence of glucose, while others were chosen for their high ratios of PAL activity in the presence of glucose to PAL activity in the absence of glucose. Retest PAL inductions were run in the absence or presence of 10 mg/ml of glucose. The results of this experiment, illustrated graphically in FIG. 2, show that in several of the isolates, a substantial improvement in the ability of the cells to produce PAL in the presence of glucose has been achieved.

Three of these isolates were particularly attractive for their ability to produce high titers of PAL in the presence of glucose. These isolates performed as follows in the tests of Example I and Example II:

| | | PAL (U/g) | | | |
|---|---|---|---|---|---|
| | | Example I | | Example II | |
| Strain | Mutagen | PA | PA + Glucose | PA | PA + Glucose |
| GX5902 | None | 46 | 37 | 70 | 54 |
| GX5903 | EMS | 163 | 71 | 74 | 92 |
| GX5904 | EMS | 33 | 33 | 82 | 62 |

EXAMPLE III

Because of the importance of genetic stability in large-scale fermentations, 2-deoxyglucose-resistance of most isolates was monitored after PAL induction. For induction, isolates were inoculated from PA+2-deoxyglucose plates into 5 ml of YPD broth, and grown for three days to a final O.D. of 5–15. This growth period was in the absence of 2-deoxyglucose, to allow expression of tendencies to revert to 2-deoxyglucose-sensitivity. After induction, the cultures in PA medium were streaked on PA+2-deoxyglucose plates and scored for growth after 7–10 days incubation. The results were as follows:

| Growth Score | Number of Isolates |
|---|---|
| +/− | 9 |
| + | 13 |
| ++ | 15 |
| +++ | 52 |

The parent R. rubra cells never showed any growth under these conditions. Most isolates therefore passed this test of genetic stability.

The genetic stability of isolate R. rubra GX5902 described in Example II was examined more closely. This strain was inoculated from a plate of PA+2-deoxyglucose into 5 ml of YPD medium and grown to stationary phase. The culture was then diluted 1,000-fold into fresh YPD, and again grown to stationary phase. This was repeated three more times. The final YPD culture was then induced for PAL in the absence and in the presence of 5 mg/ml of glucose. The observed PAL titers were 70 U/g in the absence of glucose, and 54 U/g in the presence of glucose. The activity ratio of 1.3 (i.e., 70÷54) was similar to the ratio of 1.2 originally shown by strain GX5902, and is substantially below the average ratio of 3.7 for the parent R. rubra cells. The induced culture of strain GX5902, which is estimated to have doubled about 50 times in the absence of selective pressure, was also streaked on PA+2-deoxyglucose agar. Its growth score was +++ (see above).

I claim:

1. A biologically pure culture of catabolite resistant, PAL-producing microorganism which is capable of growing on a minimal essential nutrient medium containing normally inhibiting amounts of 2-deoxyglucose and which contains, as substantially the sole carbon source, a nutritional amount of L-phenylalanine.

2. The microorganism of claim 1 which is bacterium of the genus Streptomyces or a yeast of the genus Rhodotorula, Rhodosporidium or Sporobolomyces.

3. The microorganism of claim 1 which is a strain of Rhodotorula rubra.

4. The microorganism of claim 2, which when grown on nutritional media containing L-phenylalanine in the presence and absence of normally inhibiting amounts of glucose, has a ratio of PAL production in the glucose-free medium to PAL production in the glucose medium that is less than about 2.0.

5. The microorganism of claim 4, which is a strain of Rhodotorula rubra, and in which the ratio for PAL production in the glucose-free medium to PAL production in the glucose medium is less than about 1.3.

6. The microorganism of claim 5, which has the identifying characteristics of R. rubra, strain GX-5902, NRRL-Y-15779.

7. The microorganism of claim 5, which has the identifying characteristics of R. rubra, strain GX-5903, NRRL-Y-15780.

8. The microorganism of claim 5, which has the identifying characteristics of R. rubra, strain GX-5904, NRRL-Y-15781.

9. A method for producing L-phenylalanine which comprises cultivating under growth-promoting conditions, the microorganism of claim 1, 2, 3, 4, 5, 6, 7 or 8 on a nutritional medium containing assimilable sources of carbon, nitrogen and essential minerals and growth factors; inducing the production of PAL in said microorganism by contacting it with L-phenylalanine or a PAL-inducing analog of L-phenylalanine under PAL-inducing conditions; and contacting the PAL so produced with t-cinnamic acid and ammonium ions under L-phenylalanine producing conditions.

* * * * *